United States Patent
Farver

(10) Patent No.: US 11,265,660 B2
(45) Date of Patent: Mar. 1, 2022

(54) SPEECH INTELLIGIBILITY ENHANCING SYSTEM

(71) Applicant: LIZN ApS, Vejle Øst (DK)

(72) Inventor: Niels Farver, Knebel (DK)

(73) Assignee: LIZN APS, Vejle Øst (DK)

( * ) Notice: Subject to any disclaimer, the term of this patent is extended or adjusted under 35 U.S.C. 154(b) by 0 days.

(21) Appl. No.: 16/475,822

(22) PCT Filed: Jan. 3, 2018

(86) PCT No.: PCT/DK2018/050001
§ 371 (c)(1),
(2) Date: Jul. 3, 2019

(87) PCT Pub. No.: WO2018/127263
PCT Pub. Date: Jul. 12, 2018

(65) Prior Publication Data
US 2019/0356991 A1   Nov. 21, 2019

(30) Foreign Application Priority Data

Jan. 3, 2007  (DK) ............................ PA 2017 70002

(51) Int. Cl.
*H04R 25/00* (2006.01)
*A61F 11/08* (2006.01)
(Continued)

(52) U.S. Cl.
CPC ............ *H04R 25/505* (2013.01); *A61F 11/08* (2013.01); *H03G 3/001* (2013.01); *H03G 3/3005* (2013.01);
(Continued)

(58) Field of Classification Search
CPC .......................... H04R 25/00; H04R 2225/49; H04R 2460/01; H04R 25/60; H04R 25/65; H04R 2225/023; H04R 2225/025
(Continued)

(56) References Cited

U.S. PATENT DOCUMENTS 5,550,923 A   8/1996  Hotvet
5,721,783 A   2/1998  Anderson
(Continued)

FOREIGN PATENT DOCUMENTS

EP   0993670 B1   3/2002
EP   1629808 A1   3/2006
(Continued)

OTHER PUBLICATIONS

International Preliminary Report on Patentability for corresponding application PCT/DK2018/050001 filed Jan. 3, 2018; dated Apr. 15, 2019.
(Continued)

*Primary Examiner* — Suhan Ni
(74) *Attorney, Agent, or Firm* — Cantor Colburn LLP

(57) ABSTRACT

A speech intelligibility enhancing system for difficult acoustical conditions is disclosed, the speech intelligibility enhancing system comprising at least one ear plug (201) for insertion in an ear canal (218) of a person, the at least one ear plug being arranged with an ear canal facing portion (401) and an environment facing portion (402), and the at least one ear plug comprising an acoustically attenuating path (214; 214, 213) comprising a vent (214) coupling said environment facing portion (402) with said ear canal facing portion (401); and an electroacoustic path (202, 204, 209; 202, 203, 204, 208, 209, 210, 211, 212) comprising a microphone (202) at said environment facing portion (402), a variable gain (204) and a loudspeaker (209) at said ear (Continued)

Figure 1:
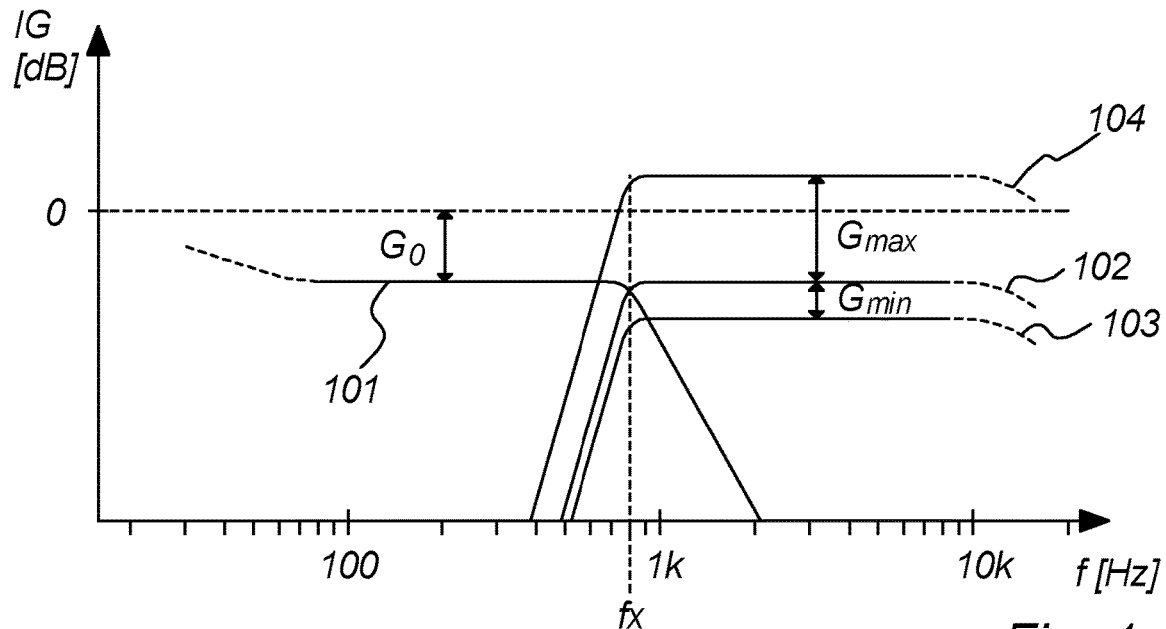

canal facing portion (401); wherein said acoustically attenuating path (214; 214, 213) is arranged with a transfer function from said environment facing portion (402) to said ear canal facing portion (401) having a low pass characteristic having a low pass cut¬off frequency and said low pass characteristic attenuating sound by a nominal attenuation (Go) for frequencies below said cut-off frequency.

20 Claims, 5 Drawing Sheets

(51) Int. Cl.
    *H03G 3/00*     (2006.01)
    *H03G 3/30*     (2006.01)

(52) U.S. Cl.
    CPC ........... *H04R 25/40* (2013.01); *H04R 25/602* (2013.01); *H04R 25/604* (2013.01); *A61F 2011/085* (2013.01); *H04R 2225/025* (2013.01); *H04R 2225/43* (2013.01); *H04R 2430/01* (2013.01); *H04R 2460/11* (2013.01)

(58) Field of Classification Search
    USPC .................. 381/312, 316–318, 320–322, 328
    See application file for complete search history.

(56) References Cited

U.S. PATENT DOCUMENTS

| | | | |
|---|---|---|---|
| 6,766,031 B1 | 7/2004 | Westermann | |
| 8,116,489 B2 * | 2/2012 | Mejia | H04R 25/505 |
| | | | 381/318 |
| 8,213,653 B2 | 7/2012 | Von Buol | |
| 8,229,127 B2 * | 7/2012 | Jorgensen | H04R 25/505 |
| | | | 381/318 |
| 2007/0030990 A1 * | 2/2007 | Fischer | H04R 25/453 |
| | | | 381/318 |
| 2007/0263891 A1 | 11/2007 | Von Buol | |
| 2009/0010442 A1 | 1/2009 | Usher | |
| 2009/0052708 A1 * | 2/2009 | Munk | H04R 25/453 |
| | | | 381/318 |
| 2009/0310805 A1 | 12/2009 | Petroff | |
| 2012/0070024 A1 | 3/2012 | Anderson | |
| 2012/0076311 A1 | 3/2012 | Isabelle | |
| 2012/0087511 A1 | 4/2012 | Lumsden | |
| 2014/0205106 A1 | 7/2014 | Linn | |

FOREIGN PATENT DOCUMENTS

| | | |
|---|---|---|
| EP | 2071872 A1 | 6/2009 |
| EP | 2434780 A1 | 3/2012 |
| WO | 2016126614 A1 | 8/2016 |
| WO | 2016189285 A1 | 12/2016 |

OTHER PUBLICATIONS

Written Opinion for corresponding application PCT/DK2018/050001 filed Jan. 3, 2018; dated Jul. 7, 2018.
International Search Report for corresponding application PCT/DK2018/050001 filed Jan. 3, 2018; dated Jul. 7, 2018.

* cited by examiner

SPEECH INTELLIGIBILITY ENHANCING SYSTEM

FIELD OF THE INVENTION

The present invention relates to enhancement of listening comfort and speech recognition especially in noisy surroundings and/or otherwise challenging acoustical conditions.

BACKGROUND OF THE INVENTION

It is a common experience that speech communication in noisy environments is difficult. Especially cocktail parties, café s and similar situations pose a challenge because the signal (the speech of a conversation partner) is very similar and often less loud than the noise (the babble of other people). A lot of mental effort is required of a person with normal hearing to discriminate words, and even more is required from a person with even a very mild hearing loss.

Many noise-suppressing algorithms (including adaptive microphone directional patterns) exhibit substantial gains in the signal-to-noise-ratio (SNR). However, they often fail to deliver better speech recognition scores in practical tests, for example due to processing artefacts and unnatural sounds.

Traditional passive hearing protectors generally attenuate too much, in particular at higher frequencies, making speech recognition even worse. Further, the traditional hearing protectors cause occlusion (i.e. a user perceives a "hollow", "muffled" or "booming" quality of his own voice due to the blocking of the ear canal without counter-acting measures).

So-called musicians ear-plugs aimed at evenly attenuating within a broad range of audio frequencies so as not to distort music perception, generally attenuates too much to be useful for understanding speech in noisy environments. They also often do not handle the occlusion effect.

Hearing aids, on the other hand, are aimed at improving audibility by using a general measure of amplifying sound. This will often not be helpful for normal hearing or near-normal hearing persons having difficulties understanding speech in a noisy environment, as described above. Further, conventional hearing aids struggle with the occlusion effect by either providing too much vent for the bone conducted sound of own voice to escape the ear canal, but thereby also preventing any attenuation of bass frequencies, or by providing too little vent thereby leading to occlusion effects when the user speaks.

An ear device directed at one or more of the above-mentioned challenges to improve listening comfort and/or speech recognition in noisy environments for normal hearing or near-normal hearing persons would be highly advantageous and useful.

SUMMARY OF THE INVENTION

The inventors have identified the above-mentioned problems and challenges in particular related to listening comfort and intelligibility of conversations in noisy environments, and subsequently made the below-described invention. The inventors have realized how to combine and apply a number of well-known research results and theories from psychoacoustics and audiology with novel features to achieve an advantageous combined technical effect and have provided a listening aid for a person to have an enhanced ability to engage in conversation with a person in front of him/her.

The present invention relates to a speech intelligibility enhancing system for difficult acoustical conditions, the speech intelligibility enhancing system comprising at least one ear plug for insertion in an ear canal of a person, the at least one ear plug being arranged with an ear canal facing portion and an environment facing portion, and the at least one ear plug comprising an acoustically attenuating path comprising a vent coupling said environment facing portion with said ear canal facing portion; and an electroacoustic path comprising a microphone at said environment facing portion, a variable gain and a loudspeaker at said ear canal facing portion; wherein said acoustically attenuating path is arranged with a transfer function from said environment facing portion to said ear canal facing portion having a low pass characteristic having a low pass cut-off frequency and said low pass characteristic attenuating sound by a nominal attenuation for frequencies below said cut-off frequency.

An advantageous effect of an embodiment of the present invention is that the vent of the acoustically attenuating path reduces the occlusion effect, even in spite of the applied attenuation from the environment facing portion to the ear canal facing portion of the acoustically attenuating path.

By an embodiment of the present invention the presentation Sound Pressure Level (SPL) is optimized for increased intelligibility. When speech is presented at very low levels, it is difficult to understand because important speech cues are not audible, which makes it hard to discriminate phonemes. As the level is increased, speech recognition increases until at some point recognition starts to deteriorate with increasing level. This phenomenon is often referred to as 'the rollover' effect. In cocktail party situations, the overall environmental SPL is usually above the rollover point. According to an embodiment, the acoustically attenuating path applies a nominal attenuation, thereby increasing the intelligibility of loud speech, or speech in noisy environments. Further, according to an embodiment, the electroacoustic path may also apply a negative gain to increase intelligibility of speech.

An advantageous feature of the present invention is the passive processing of bass, whereby frequencies below the low pass cut-off frequency are attenuated acoustically. Many conventional noise-suppressing algorithms (including adaptive microphone directional patterns) exhibit substantial gains in SNR. However, they often fail to deliver better speech recognition scores in practical tests, because these algorithms are prone to produce 'glitches' or unnatural sounds that attract the user's attention thereby reducing focus on or even masking the speech to be recognized. This is avoided by the present invention.

The present invention is advantageous by facilitating prolonged stay in noisy or otherwise loud environments by applying a slight general attenuation. For example, a general attenuation of 3 dB may reduce the noise exposure by 50%, or alternatively allow the wearer to stay twice as long in a situation for the ears to be subjected to the same noise exposure as would be the case without the system.

To further increase protection against exposure to loud sounds, it is advantageous to include means for limiting the peak SPL delivered to the ear canal. This may be done in either the acoustically attenuating path, in the electroacoustic path or both. Said peak limiting means may include acoustical mechanisms, such as implemented by narrow slots, electromechanical, such as implemented using thin membranes with limited movement. Further, electro-acoustical means may be employed, such as simply reducing the electrical gain when loud sounds are detected and/or by emitting a phase reversed replica of a sound to be attenuated via the loudspeaker.

Noise induced hearing loss is often most prominent around 3 kHz due to the resonance of the open ear canal. It is therefore especially advantageous to include a gain reduction mechanism that limits the power transmitted to the ear around 3 kHz.

In an embodiment, said nominal attenuation is in the range of 2 dB to 10 dB at 500 Hz, such as in the range of 2 dB to 8 dB at 500 Hz, such as in the range of 2 dB to 6 dB at 500 Hz, such as in the range of 2 dB to 5 dB at 500 Hz, such as in the range of 3 dB to 5 dB at 500 Hz, such as in the range of 3 dB to 4 dB at 500 Hz.

In an embodiment, said low pass cut-off frequency is in the range of 600 Hz to 1200 Hz, such as 700 Hz to 1000 Hz, such as 750 Hz to 900 Hz, such as 800 Hz, the low pass cut-off frequency being the 3 dB corner frequency.

In an embodiment, said low pass characteristic is essentially flat from 50 Hz to said cut-off frequency.

In an embodiment, said electroacoustic path is arranged with a transfer function from said environment facing portion to said ear canal facing portion having a high pass characteristic having a high pass cut-off frequency and wherein said electroacoustic path is arranged to apply a high pass gain for frequencies above said high pass cut-off frequency.

According to the invention, a variable gain designates a signal processing block having a controllable gain, thereby enabling that the electroacoustic path applies a high pass gain. It is noted that the gain may be negative or positive.

According to an embodiment of the invention, the application of a high pass gain in relation to the system facilitates a low energy consumption, an advantageous use of loudspeakers, etc.

According to an embodiment of the invention, the application of a low pass characteristic facilitates less masking of high frequency components processed by said electroacoustic path.

In an embodiment, said low pass cut-off frequency and said high pass cut-off frequency establishes a crossover frequency between said acoustically attenuating path and said electroacoustic path.

The use of the two different types of paths facilitates establishment of a hybrid transfer function through the combination of the transfer function of the electroacoustic path and the transfer function of the acoustically attenuating path. An advantageous effect of the combined transfer function is that the control algorithm of the system may focus solely on the controlling of frequencies above the crossover frequency.

In an embodiment, said high pass gain is controllable between a minimum gain and a maximum gain.

In an embodiment, said high pass gain is in the range of −30 dB to +20 dB at 3 kHz, such as in the range of −25 dB to +15 dB at 3 kHz, such as in the range of −20 dB to +10 dB at 3 kHz.

In an embodiment, said high pass cut-off frequency is in the range of 600 Hz to 1200 Hz, such as 700 Hz to 1000 Hz, such as 750 Hz to 900 Hz, such as 800 Hz, the high pass cut-off frequency being the 3 dB corner frequency.

In an embodiment, said high pass characteristic is essentially flat from said cut-off frequency at least to 5 kHz, such 7 kHz.

In an embodiment, said earplug comprises a gain controller arranged to control said variable gain.

In an embodiment, said controlling said variable gain is based on a signal from said microphone.

In an embodiment, said controlling said variable gain is based on a level of a signal from said microphone.

In an embodiment, said electroacoustic path comprises a microphone preamp and filter.

In an embodiment, at least one of said transfer function of the electroacoustic path and said transfer function of the acoustically attenuating path comprises an open-ear resonance compensation gain.

Inserting an ear plug in the ear canal changes the natural frequency response of the open-ear, most noticeable around the open-ear resonance around 3 kHz. In an advantageous embodiment, this change is compensated by applying a similar gain at that frequency. The compensation may for example be applied at the microphone preamp, the variable gain, between the variable gain and the loudspeaker, or acoustically in the path from loudspeaker to ear canal.

In an embodiment, said gain controller is implemented digitally and an analog-to-digital converter is provided between said microphone and said gain controller.

In an embodiment, said variable gain has a digital control input connected to said gain controller.

In an embodiment, said microphone is a directional microphone, such as a hypercardiod microphone.

Using a directional microphone may improve the signal-to-noise-ratio (SNR) significantly. Several studies have shown that the use of directional microphones in hearing aids is the single most effective and reliable way to improve the signal-to-noise ratio and thereby the speech recognition in a cocktail-party situation. Although a preferred embodiment of the present invention only reproduces the microphone signal at frequencies above said crossover frequency, the use of a directional microphone still improves the SNR of the embodiment.

In an embodiment, said variable gain is analog.

In an embodiment, said gain controller is digital.

In an embodiment, said loudspeaker is an electrodynamic loudspeaker.

In an embodiment, said ear plug is battery powered, such as powered by a rechargeable battery.

In an embodiment, the system comprises peak limiting means, such as a peak limiter system, for attenuating loud sounds. This is advantageous to increase the protection of the user against exposure to loud sounds. The peak limiting means are arranged to limit the peak sound pressure level (SPL) delivered to the ear canal.

In an embodiment, the peak limiting means, e.g. peak limiting system, comprises a peak limiter arranged in said acoustically attenuating path. This may advantageously by implemented by providing one or more narrow slots in said vent to limit the amount of acoustic power that can be conducted through the vent.

In an embodiment, said peak limiting means, e.g. peak limiting system, comprises a peak limiter arranged in said electroacoustic path. This may be implemented by an electromechanical peak limiter arranged in said microphone and/or said loudspeaker, for example by limiting the membrane excursion of the microphone or the loudspeaker. Alternatively, a peak limiter in the electroacoustic path may advantageously be implemented by an electronic peak limiter arranged to apply an attenuation to sounds received by said microphone having a level exceeding a predetermined peak limitation threshold, and/or arranged to produce by said loudspeaker a phase reversed replica of sounds received by said microphone having a level exceeding a predetermined peak limitation threshold.

In an embodiment, said peak limiting means, e.g. peak limiting system, for attenuating loud sounds is arranged with a maximum attenuation around a frequency of 3 kHz. The peak limitation, i.e. the protection against noise induced hearing loss by limiting the power transmitted to the ear, is advantageously focused on the resonance frequency of the open ear canal, as noise induced hearing loss is often most prominent at this frequency.

In an embodiment, said at least one ear plug comprises two ear plugs, one for each ear canal of the person, and wherein said two ear plugs are arranged to coordinate settings between them.

THE DRAWINGS

Figure 2:
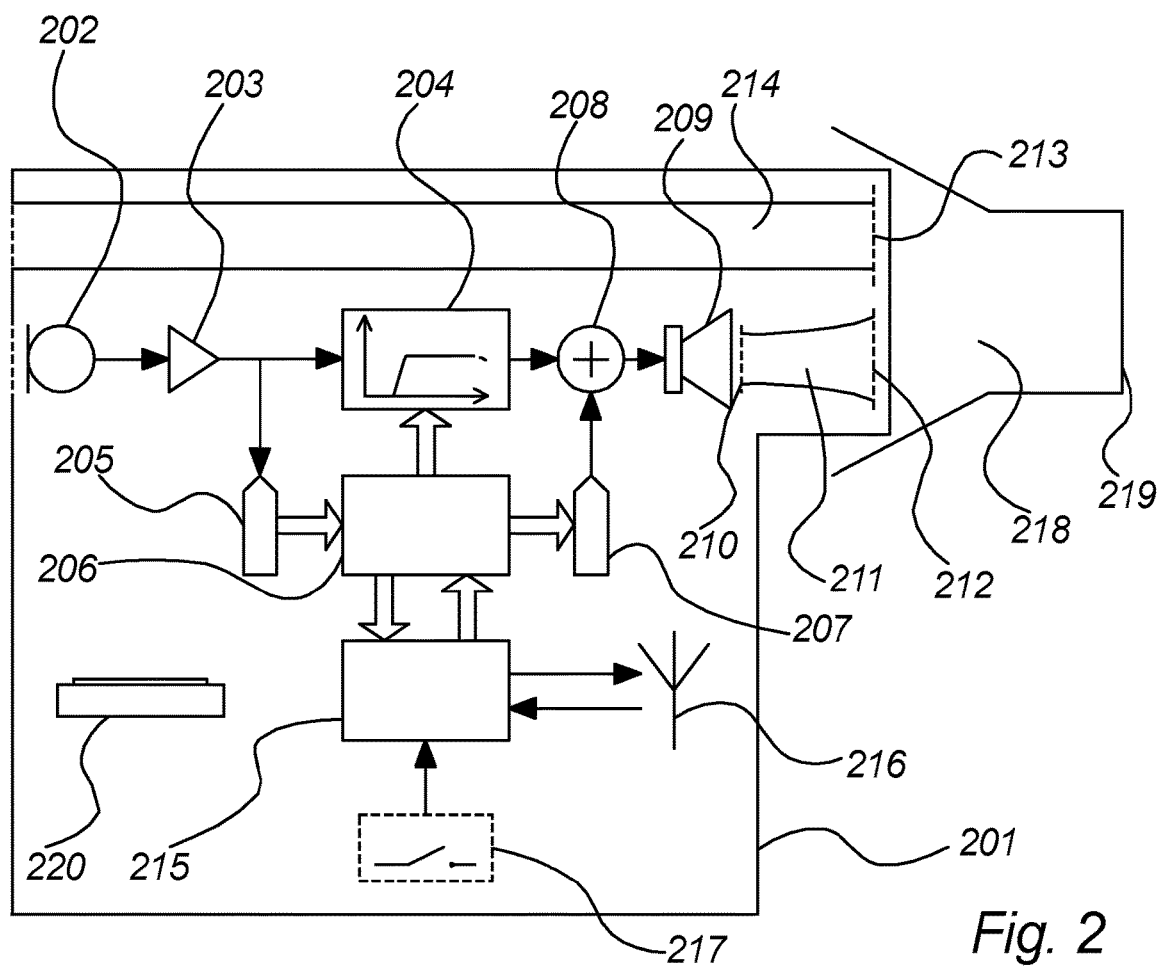
Figure 3:
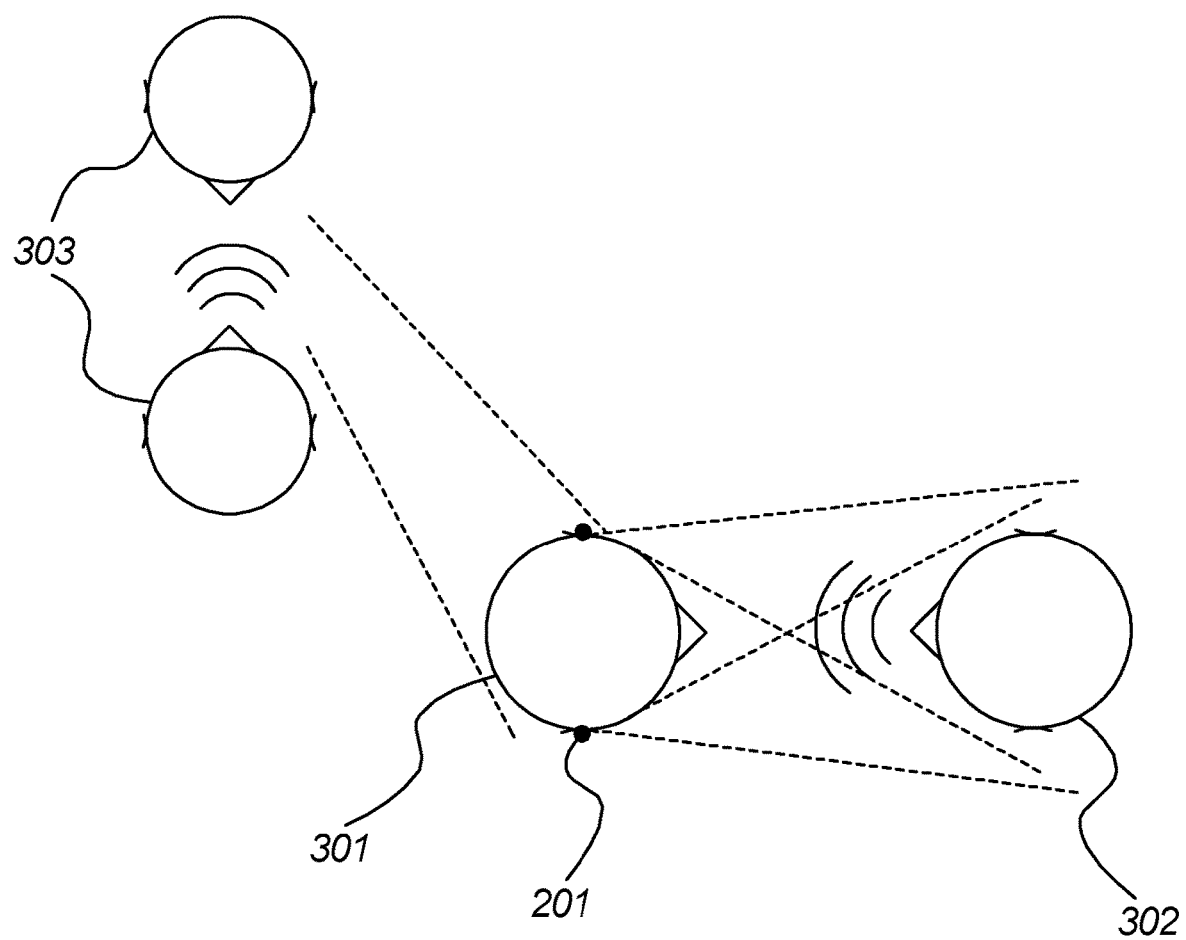
Figure 4:
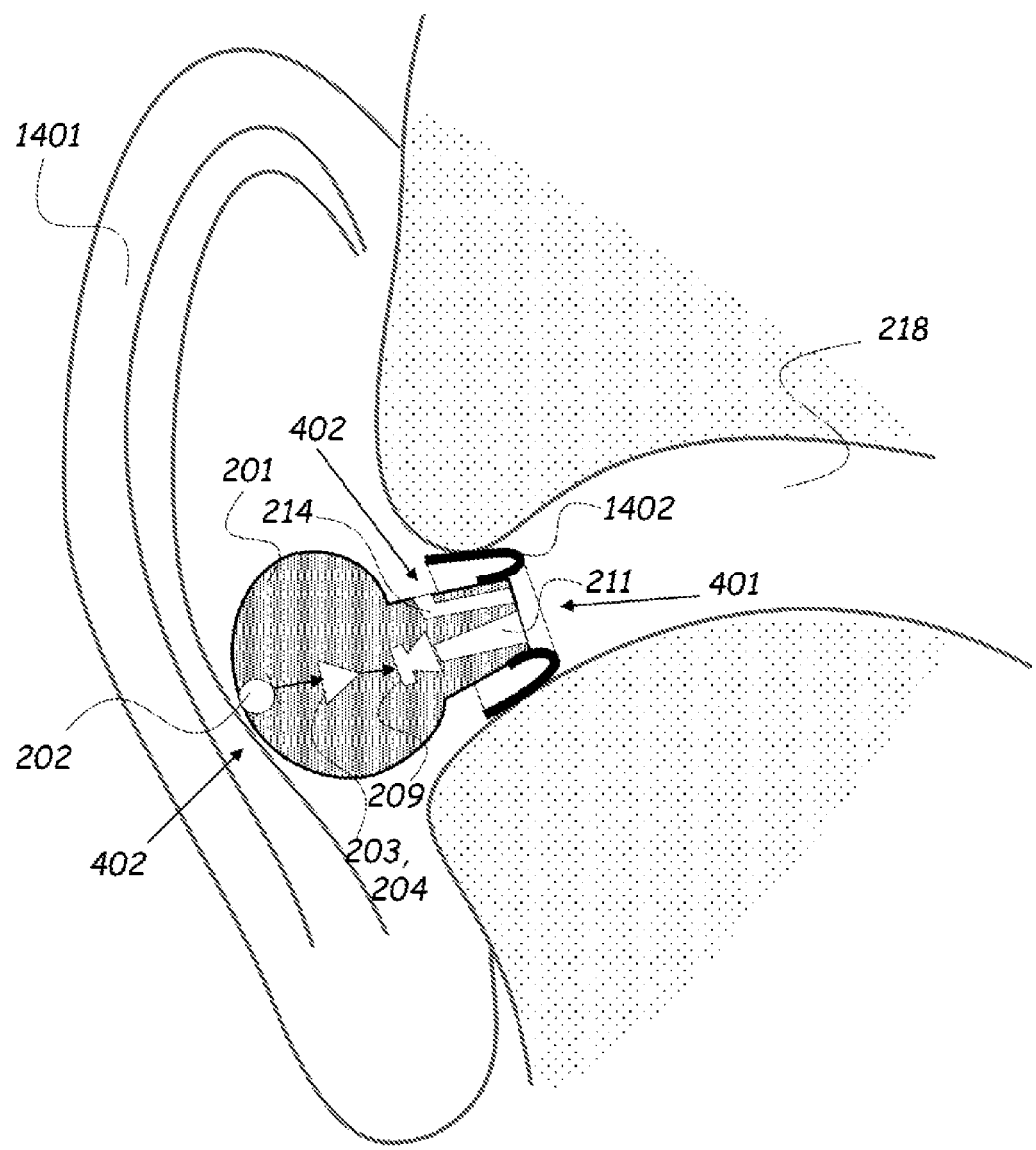
Figure 5A:
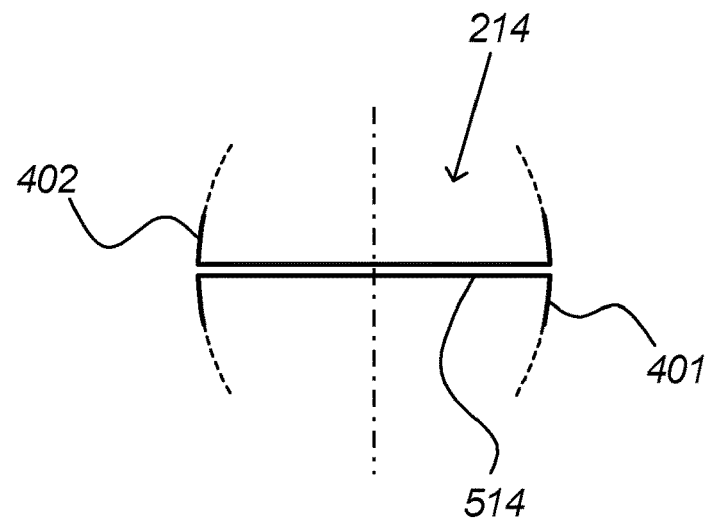
Figure 5B:
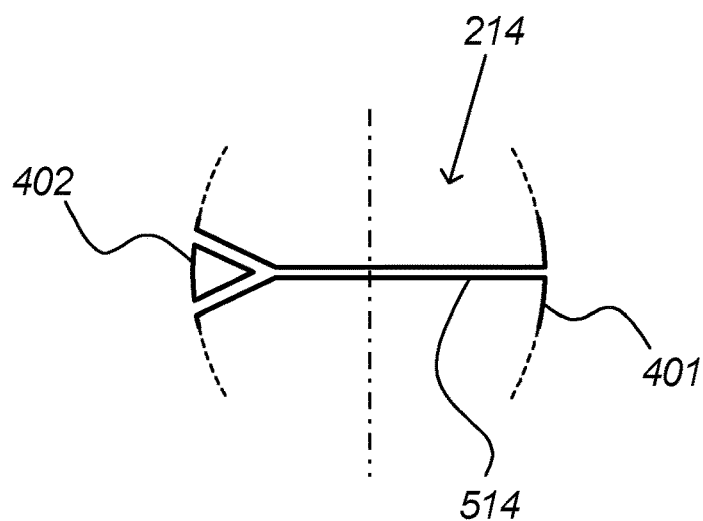
Figure 5C:
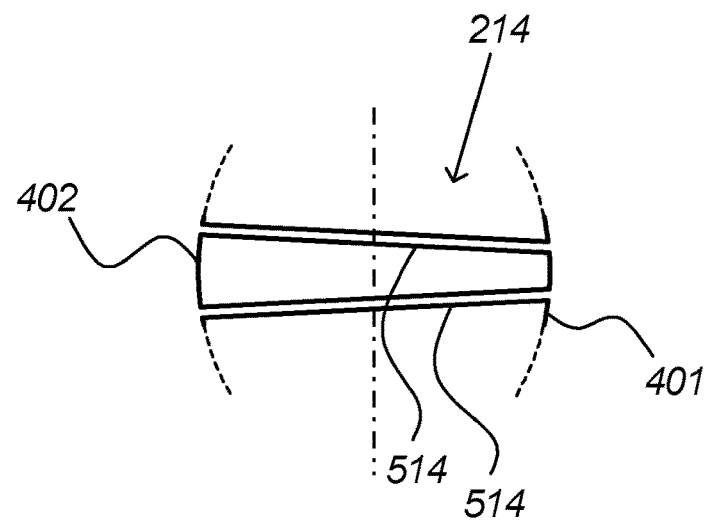
Figure 6:
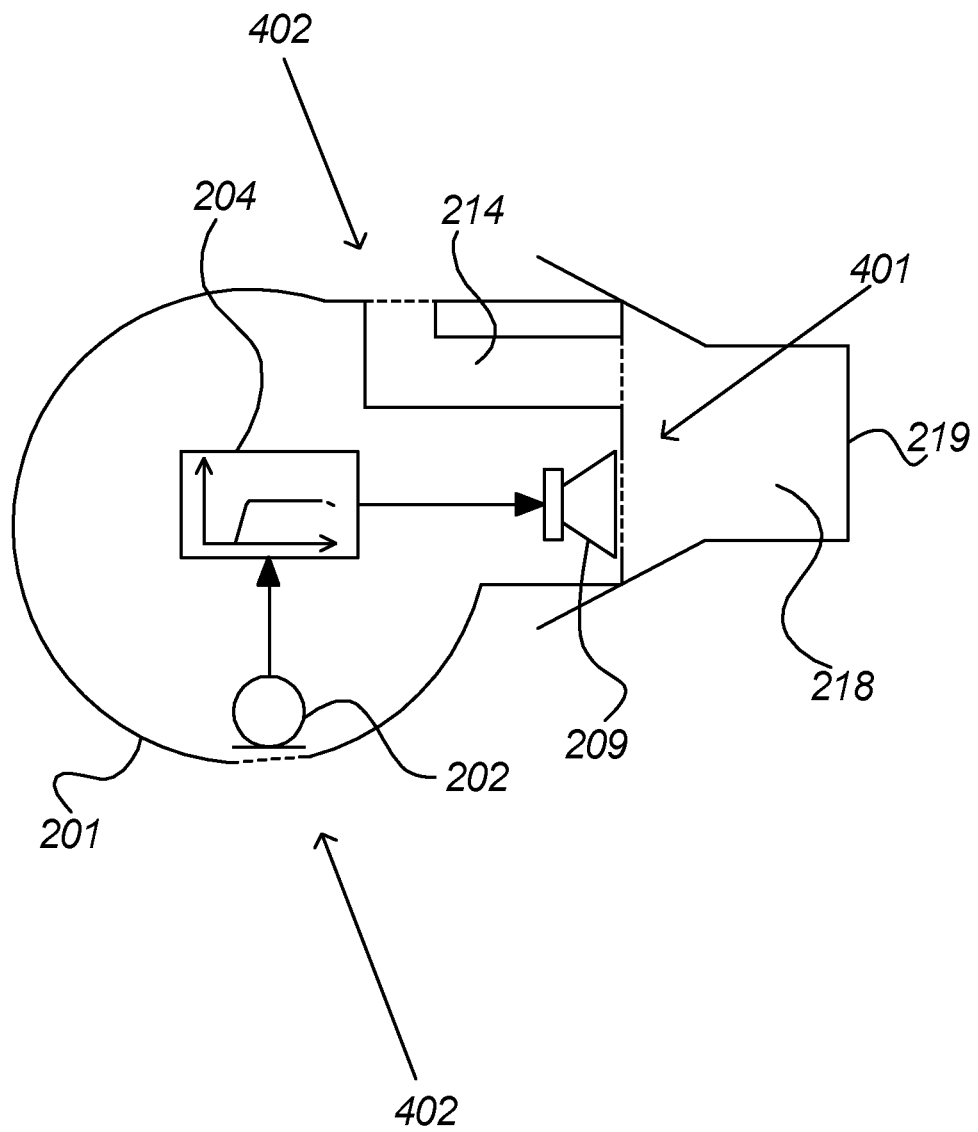

The invention will in the following be described with reference to the drawings where FIG. 1 is a plot illustrating insertion gain versus frequency for the vent path and the variable gain path according to an embodiment of the invention, FIG. 2 illustrates a block diagram of an embodiment of a speech intelligibility enhancing system according to the invention, FIG. 3 shows a typical usage scenario, FIG. 4 illustrates an earplug according to an embodiment of the invention inserted in an ear canal, FIG. 5 illustrates vent configurations according to embodiments of the inventions, and FIG. 6 illustrates an overview block diagram of an embodiment of the invention.

DETAILED DESCRIPTION

FIG. 6 illustrates an overview block diagram of an embodiment of the invention. It comprises an earplug 201 inserted in an ear canal 218 of a person. The ear canal ends at the tympanic membrane 219. The ear plug 201 has an ear canal facing portion 401 and an environment facing portion 402. The boundary between ear canal facing portion and environment facing portion is at the circumference of the ear plug where it generally is in contact with the ear canal, i.e. substantially plugs the ear canal.

The ear plug 201 comprises an acoustically attenuating path 214 comprising a vent 214 acoustically coupling the environment to the ear canal by a low pass transfer function attenuating the passband below the low pass cut-off frequency for example between 2 dB and 10 dB, as explained in more detail below.

The ear plug 201 also comprises an electroacoustic path comprising a microphone 202, preferably a directional microphone, a variable gain 204, i.e. a signal processing block with controllable gain, and a loudspeaker 209. The electroacoustic path facilitates reproduction of sounds from the environment in the ear canal 218.

FIG. 1 is a plot illustrating insertion gain versus frequency for the acoustically attenuating path and the electroacoustic path according to an embodiment of the invention. The insertion gain IG of 0 dB corresponds to the transfer function from environment to the tympanic membrane 219 with open ear canal, i.e. without an ear plug inserted. The illustrated insertion gain curves 101, 102, 103, 104, shows the difference to the open ear situation achieved by inserting the ear plug 201, with the curve 101 illustrating the insertion gain achieved by the acoustically attenuating path, and the curves 102, 103 and 104 illustrating various insertion gains obtainable by the electroacoustic path.

The acoustically attenuation path applies a transfer function 101 with a low pass characteristic with a cut-off frequency of about 800 Hz. The low pass characteristic is substantially flat in a band from about 50 Hz to the cut-off frequency, but with a nominal attenuation $G_0$ of between 2 dB and 10 dB, e.g. 3-4 dB. Hence, compared to the open ear scenario, the vent 214 causes a general attenuation of bass and a significant blocking of sound components above the cut-off frequency.

The electroacoustic path applies a transfer function with variable gain 102, 103, 104, with a high pass characteristic with a cut-off frequency of about 800 Hz, i.e. substantially equal to the cut-off frequency of the acoustic low pass filter. The high pass characteristic is substantially flat in a band from about the cut-off frequency to, e.g. 5 kHz, 7 kHz or higher. The variable gain 102 at the flat band may for example be set to match the nominal attenuation $G_0$ of curve 101 to present in combination a natural frequency response of environmental sounds but at a generally reduced sound pressure level (SPL). The variable gain may in another situation be reduced further, e.g. to a minimum gain $G_{MIN}$ according to curve 103 to allow the user to rest or protect his or her ears. The variable gain may in a situation of for example conversation be set to an increased gain, e.g. in accordance with curve 104, to emphasize consonants and improve speech intelligibility.

FIG. 2 illustrates a block diagram of an embodiment of a speech intelligibility enhancing system according to the invention. The system comprises one or two ear plugs 201 suitable for inserting in a person's ear canal(s) 218.

Each ear plug 201 has an outer shape to generally block the ear canal, but comprises a vent 214 acoustically coupling the ear canal 218 to the environment of the person. The vent may be provided with a vent damping cloth 213 in either or both ends, here shown in the ear canal end of the vent. The vent 214 is arranged to allow environmental sound to reach the tympanic membrane 219 of the person, however at an attenuated level. The attenuation provided by the vent 214 is preferably frequency-dependent, preferably as a low pass filter, preferably in accordance with the vent attenuation curve 101 of FIG. 1.

A vent cut-off frequency $f_x$ of the vent attenuation curve 101 may for example be located in the interval of 600 Hz to 1200 Hz, for example around 800 Hz, below which the vent 214 applies a nominal attenuation $G_0$ of for example between 3 dB and 9 dB, preferably around 3 dB. Above the vent cut-off frequency, the vent attenuation curve rolls off, thereby blocking higher frequencies.

The attenuating vent may be realized in a number of ways commonly known to those skilled in the art using combinations of damping material or damping cloth and conduit segments of varying diameter. It is a design objective to have essentially frequency independent attenuation between 2 dB and 10 dB in the frequency range from 50 Hz up to the cut-off frequency while at the same time maintaining an essentially low input impedance of the vent as seen from the ear canal facing portion 401. In order to keep the design simple and compact, a trade-off must be made between the vent's beneficial effect on occlusion and its attenuation of sound transmitted from the environment facing portion 402 to the ear canal facing portion. In a preferred embodiment it has been found that attenuation of around 4 dB can be achieved while maintaining a subjectively acceptable impression of the occlusion effect.

Although the vent 214 preferably is established as one conduit, e.g. having a length of 5 mm and a diameter of 1.5 mm, it may in alternative embodiments be established as a combination of two or more conduits. The conduit(s) may be branched in either or both ends. The holes in the ends of the conduits may have same of different diameters compared to the conduit diameter, and may be covered by damping cloth 213 in either or both ends for applying damping and/or for avoiding the conduits getting clogged by debris. Examples of vent embodiments are illustrated in FIGS. 5A-5C, where a vent 214 is formed by one or more conduits 514. One conduit 514 in FIG. 5A, two conduits 514 in FIG. 5C, and a branched conduit 514 in FIG. 5B. It is noted that the branched conduit can be branched in either or both ends, and in two or more branches. The vents 214 in the figures extends from an environment facing portion 402 of the ear plug 201 to an ear canal facing portion 401 of the ear plug 201.

The acoustically attenuating path 214 may in an embodiment further comprise peak limiting means, for example implemented by narrow slots, to provide protection for the user against exposure to loud sounds. This may be combined with further means for peak SPL limitation implemented in the electroacoustical path as described below.

In addition to the vent 214, each ear plug 201 comprises a microphone 202, a variable gain 204 and a loudspeaker 209, thereby establishing an alternative path for audio between the environment and the ear canal 218. As described above with reference to FIG. 1, this alternative path provides a variable gain, preferably implemented as a high pass filter, preferably having a cut-off frequency in the same range as the cut-off frequency of the vent 214, thereby applying a variable gain to frequencies above that frequency, as illustrated in FIG. 1.

In a preferred embodiment, the cut-off frequencies of the low pass vent 214 and of the high pass variable gain 204 are preferably close, e.g. less than 100 Hz apart, preferably less than 50 Hz apart, and may thus be denoted a crossover frequency $f_x$.

The microphone 202 is coupled to the person's environment outside the ear canal 218, and may comprise any sound sensitive device, for example one or more miniature electret microphones. The microphone 202 may preferably comprise a directional microphone, e.g. one or more transducer elements arranged with sound conduits so as to provide a directional sensitivity pattern of e.g. hyper-cardioid shape, as well-known to the person skilled in microphone design.

The variable gain 204 may for example be implemented using a multiplying digital-to-analog converter, or some other form of a programmable gain amplifier, e.g. an amplifier with switched feed-back.

In a preferred embodiment, the audio path from microphone 202 via variable gain 204 to loudspeaker 209 is a low latency path to avoid delay between the acoustic vent path 214 and the electric variable gain path 204 as much as possible. The variable gain 204 is therefore preferably implemented as an analog design, e.g. with switched feedback, because fast digital designs have significantly higher energy consumption and/or price.

The loudspeaker 209 is arranged in the ear plug 201 so that it produces sound in the ear canal 218 based on the output of the variable gain 204. Preferably a loudspeaker duct 211 with loudspeaker duct entry damping cloth 210 and/or loudspeaker duct exit damping cloth 212 is provided between the loudspeaker 209 and the ear canal 218, to avoid undesired resonances. The vent damping cloth 213 and the loudspeaker duct exit damping cloth 212 may comprise a common damping cloth. The loudspeaker may comprise one or more electroacoustic transducers producing sound from electric signals, for example a piezoelectric loudspeaker, a balanced armature receiver or preferably an electro-dynamic loudspeaker.

A microphone preamp and filter 203 may be provided for conditioning the microphone signal, for example with respect to frequency response, equalization etc. For example, the microphone filter 203 may compensate for non-ideal microphone frequency response and/or add equalization to compensate for the open-ear canal resonance, which is modified when the ear plug is inserted.

Equalisation to compensate for the modified ear canal resonance should be incorporated in the system, but may be implemented at various places in the signal path as convenient. In a preferred embodiment the boost at 3 kHz is implemented using electronic filtering established around the output amplifier stage for the loudspeaker 209. In another preferred embodiment a suitable resonance is created by tuning air volumes close to the loudspeaker membrane as well as the shape of the sound duct 211.

A variable gain controller 206 is provided to control the variable gain 204. As illustrated in FIG. 2, the variable gain controller 206 is preferably implemented using a software module running on a digital controller, e.g. an ARM Cortex-MO processor. Although the main channel with variable gain 204 is preferably an analog channel as described above, the side-channel may preferably be implemented in the digital domain to allow for a compact, programmable implementation, preferably integrating all required sub-systems, for example analog-to-digital converter 205, digital-to-analog converter 207, the variable gain controller 206, a system controller 215, and input/output channels for further components. The processor may even comprise a built-in communication interface 216, for example a Bluetooth wireless communication interface. In an alternative embodiment, the side-chain is analog as the main channel. In an alternative embodiment, the main channel, in particular the variable gain, is also implemented by a software module in the processor.

The variable gain controller 206 is arranged to receive and analyze the audio signal from the microphone, and on the basis thereof control the variable gain 204. In an embodiment, the sampling rate of the analog-to-digital converter 205 needs not satisfy usual audio requirements as the sampled signal is merely used for control, whereas it is the preferably analog signal of the main channel which is processed by the variable gain 204 and forwarded to the loudspeaker 209. In an embodiment, the sample rate of the analog-to-digital converter 205 may for example be in the range of 8 kHz to 24 kHz.

In an embodiment, the gain controller 206 controls the operating mode and variable gain 204 based on a level and/or content of the microphone signal. For example, an operating mode of general attenuation may be selected based on determining a microphone signal of generally loud noise and no speech components. For example, an operating mode of periodic positive gain may be selected when determining a speech signal at a general background noise level below a predetermined threshold, to improve speech intelligibility by emphasizing consonants. For example, an operating mode of generally increased positive gain may be selected when determining a speech signal in a very loud and noisy environment, where periodic emphasizing of consonants may be impossible because of several conversations or consonant-like sounds being intercepted.

The gain of the variable gain 204 is in a preferred embodiment controlled by the variable gain controller 206 on the basis of a heuristic model using a short-time power spectrum of the microphone signal as input. In a preferred embodiment, the variable gain controller 206 is arranged to detect certain conditions, e.g. when modulation spectra fulfill certain criteria, and in response thereto utilize the variable gain 204 in different ways, e.g. as a syllabic compressor to make consonants stand out. This may for example be advantageous for enhancing speech intelligibility, but may cause other audio categories, e.g. music, to sound unnatural. The certain conditions detected by the variable gain controller may, for example, relate to different audio categories, e.g. to distinguish between speech and other sounds, or more categories, e.g. speech, music and noise, or even more categories, such as distinguishing between individual sound units of speech, e.g. vowel type units and consonant type units, so as to be able to change a variable gain control mode in dependency of the currently received audio category. In a preferred embodiment, for example, the above-mentioned syllabic compression may be applied to make consonants stand out, but only when relevant consonants are detected or are likely to occur. Even with relatively low sampling frequency in the side-chain and no delay in the main channel, the unit rate of speech is sufficiently slow to leave time to change mode and emphasize the remaining of a specific speech unit leading to significant improvement of intelligibility.

A system controller 215 is provided in a preferred embodiment for overall control of the various system parts. As mentioned above, the system controller 215 is preferably integrated in the same processor implementing the variable gain controller 206, but may in other embodiments be implemented as a separate processor or simpler logic circuit. The system controller may for example be arranged to control switching on and off, changing of mode and/or parameters, monitoring battery power and charging, etc.

In a preferred embodiment, the system comprises a wireless communication interface 216, preferably a Bluetooth Low Energy interface, or other wireless communication technology.

The communication interface 216 may for example be used to receive streaming audio, e.g. from a smartphone, e.g. music or a telephone conversation, which may be processed by system controller 215 and variable gain controller 206 and injected in the main audio channel by digital-to-analog converter (DAC) 207 and summing point 208 to be rendered by the loudspeaker 209.

In an embodiment, the speech intelligibility enhancement system comprises two ear plugs 201, one for each ear canal of a person, and the communication interface 216 is used for the two ear plugs to communicate settings and parameters. Thereby is also facilitated synchronized changes of gain or mode in both ear plugs.

In an embodiment, most side chain processing is performed in one earplug and the resulting mode and parameter changes transferred to be used in the ear plug of the opposite ear canal, thereby reducing the collective energy consumption of the ear plugs.

The wireless communication interface 216 may also or instead be used for remote control of the ear plug.

In an embodiment, the ear plug 201 comprises a connector for a wired connection to a device, e.g. a smartphone, e.g. for transferring audio and/or data to be rendered by the system.

In a preferred embodiment, the system controller 215 is communicatively coupled to a user interface 217, e.g. via an analog or digital input channel of the processor. The user interface 217 may preferably comprise a capacitive sensor for touch control, but may also or instead comprise a switch, a pushbutton, a light sensitive device, etc. The user interface may alternatively or in addition comprise a remote control input of any remote control technology such as infrared or radio frequency based remote control, etc. The user interface 217, in a preferred embodiment a single touch sensitive area of the outer part of the ear plug 201, may for example be used to change mode of the device, e.g. between a speech enhancing mode for listening to conversations and a headphone mode for streaming music or telephone calls from a connected smartphone or other device, and an ear resting mode applying maximum attenuation to protect the hearing as much as possible.

In an embodiment, the DAC 207 is also used to provide system messages and/or feedback to user interaction into the ear of the user.

Each ear plug 201 preferably comprises a rechargeable battery 220 for powering the electronics.

The electroacoustic path may in an embodiment further comprise peak limiting means to provide protection for the user against exposure to loud sounds, for example implemented by mechanical limitations of the microphone and/or loudspeaker membranes, or for example implemented electronically by reducing the electrical gain when loud sounds are detected and/or by emitting a phase reversed replica of a sound to be attenuated via the loudspeaker. This may be combined with further means for peak SPL limitation implemented in the acoustically attenuating path as described above.

FIG. 3 shows a typical usage scenario, for example the above-mentioned cocktail party scenario, where a listening person 301 is trying to hear speech of a speaking person 302, while being disturbed by background noise 303, here illustrated in the form of conversations between other persons. The listening person 301 is wearing earplugs 201 of an embodiment of the present invention, and thereby perceives improved speech intelligibility.

FIG. 4 illustrates an earplug 201 according to an embodiment of the invention inserted in an ear canal 218. The earplug 201 preferably rests in the outer ear 1401 of the person, and is provided with a flexible ear tip 1402 for providing acoustic sealing in ear canals of different users. The contact of the ear tip 1402 with the ear canal 218 defines a boundary between an ear canal facing portion 401 and an environment facing portion 402 of the ear plug 201. The earplug comprises a vent 214 acoustically coupling the environment with the ear canal. An electroacoustic path comprising a microphone 202 at the environment facing portion 402, a preamp 203, a variable gain 204 and a loudspeaker 209 is provided within the ear plug, and a loudspeaker duct 211 is provided at the ear canal facing portion 401 of the earplug.

LIST OF REFERENCE SIGNS

In the above description, the following signs are used to refer to the drawings:

IG Insertion gain
$f_x$ Crossover frequency
$G_0$ Nominal attenuation
$G_{MAX}$ Maximum gain
$G_{MIN}$ Minimum gain
101 Acoustically attenuating path gain curve
102 Electroacoustical path gain curve, neutral
103 Electroacoustical path gain curve, minimum
104 Electroacoustical path gain curve, maximum
201 Ear plug
202 Microphone
203 Microphone preamp and filter
204 Variable gain
205 Analog-to-digital converter
206 Variable gain controller
207 Digital-to-analog converter
208 Summing point
209 Loudspeaker 210 Loudspeaker duct entry damping cloth
211 Loudspeaker duct
212 Loudspeaker duct exit damping cloth
213 Vent damping cloth
214 Vent
215 System controller
216 Communication interface
217 User interface
218 Ear canal
219 Tympanic membrane
220 Battery
301 Listening person (Wearer/User)
302 Speaking person (Conversation partner)
303 Background noise (Competing speech)
401 Environment facing portion
402 Ear canal facing portion
514 Vent conduit
1401 Pinna (outer ear)
1402 Flexible ear tip providing acoustic sealing

The invention claimed is:

1. A speech intelligibility enhancing system for difficult acoustical conditions, the speech intelligibility enhancing system comprising:
at least one ear plug for insertion in an ear canal of a person, the at least one ear plug being arranged with an ear canal facing portion and an environment facing portion, and the at least one ear plug comprising:
an electroacoustic path comprising a microphone at said environment facing portion, a variable gain and a loudspeaker at said ear canal facing portion; and
an acoustically attenuating path comprising a vent coupling said environment facing portion with said ear canal facing portion;
wherein said acoustically attenuating path is arranged with a transfer function from said environment facing portion to said ear canal facing portion having a low pass characteristic having a low pass cut-off frequency and said low pass characteristic attenuating sound by a nominal attenuation for frequencies below said cut-off frequency; and
wherein said nominal attenuation is in the range of 2 dB to 10 dB at 500 Hz and said low pass cut-off frequency is in the range of 600 Hz to 1200 Hz, the low pass cut-off frequency being the 3 dB corner frequency.

2. The system according to claim 1, wherein said vent comprises a vent damping cloth in at least one end of said vent.

3. The system according to claim 2, wherein said vent comprises a vent damping cloth in both ends of said vent.

4. The system according to claim 1, wherein said low pass characteristic is essentially flat from 50 Hz to said cut-off frequency.

5. The system according to claim 1, wherein said electroacoustic path is arranged with a transfer function from said environment facing portion to said ear canal facing portion having a high pass characteristic having a high pass cut-off frequency and wherein said electroacoustic path is arranged to apply a high pass gain for frequencies above said high pass cut-off frequency.

6. The system according to claim 1, wherein said low pass cut-off frequency and said high pass cut-off frequency establishes a crossover frequency between said acoustically attenuating path and said electroacoustic path.

7. The system according to claim 1, wherein said high pass gain is in the range of −30 dB to +20 dB at 3 kHz and said high pass cut-off frequency is in the range of 600 Hz to 1200 Hz, the high pass cut-off frequency being the 3 dB corner frequency.

8. The system according to claim 1, wherein said high pass characteristic is essentially flat from said cut-off frequency at least to 5 kHz.

9. The system according to claim 1, wherein said earplug comprises a gain controller arranged to control said variable gain based on a signal from said microphone.

10. The system according to claim 9, wherein said gain controller is implemented digitally and an analog-to-digital converter is provided between said microphone and said gain controller.

11. The system according to claim 9, wherein said variable gain has a digital control input connected to said gain controller.

12. The system according to claim 1, wherein at least one of said transfer function of the electroacoustic path and said transfer function of the acoustically attenuating path comprises an open-ear resonance compensation gain.

13. The system according to claim 1, wherein said microphone is a directional microphone.

14. The system according to claim 1, wherein said variable gain is analog.

15. The system according to claim 1, wherein said loudspeaker is an electrodynamic loudspeaker.

16. The system according to claim 1, wherein said ear plug is battery powered.

17. The system according to claim 1, comprising a peak limiting system comprising a peak limiter arranged in said acoustically attenuating path.

18. The system according to claim 1, comprising a peak limiting system comprising a peak limiter arranged in said electroacoustic path.

19. The system according to claim 1, comprising a peak limiting system for attenuating loud sounds arranged with a maximum attenuation around a frequency of 3 kHz.

20. The system according to claim 1, wherein said at least one ear plug comprises two ear plugs, one for each ear canal of the person, and wherein said two ear plugs are arranged to coordinate settings between them.

* * * * *